United States Patent
Jones et al.

(10) Patent No.: US 9,040,021 B2
(45) Date of Patent: May 26, 2015

(54) HETEROCYCLIC COMPOUNDS AS IMAGING PROBES OF TAU PATHOLOGY

(75) Inventors: Clare Jones, Amersham (GB); Amanda Ewan, London (GB); Duncan Wynn, Amersham (GB); Alessandra Gaeta, Amersham (GB); James Nairne, Amersham (GB)

(73) Assignee: GE Healthcare Limited, Buckinghamshire (GB)

( * ) Notice: Subject to any disclaimer, the term of this patent is extended or adjusted under 35 U.S.C. 154(b) by 0 days.

(21) Appl. No.: 13/885,466

(22) PCT Filed: Nov. 7, 2011

(86) PCT No.: PCT/US2011/059495
§ 371 (c)(1),
(2), (4) Date: May 15, 2013

(87) PCT Pub. No.: WO2012/067863
PCT Pub. Date: May 24, 2012

(65) Prior Publication Data
US 2013/0236395 A1    Sep. 12, 2013

Related U.S. Application Data

(60) Provisional application No. 61/414,007, filed on Nov. 16, 2010.

(51) Int. Cl.
| | | |
|---|---|---|
| *A61K 51/00* | (2006.01) | |
| *A61M 36/14* | (2006.01) | |
| *A61K 51/04* | (2006.01) | |
| *C07D 215/12* | (2006.01) | |
| *C07D 215/14* | (2006.01) | |
| *C07D 215/18* | (2006.01) | |
| *C07D 215/36* | (2006.01) | |
| *C07D 295/067* | (2006.01) | |
| *C07D 401/04* | (2006.01) | |
| *C07D 401/12* | (2006.01) | |

(52) U.S. Cl.
CPC .......... *A61K 51/0455* (2013.01); *C07D 215/12* (2013.01); *C07D 215/14* (2013.01); *C07D 215/18* (2013.01); *C07D 215/36* (2013.01); *C07D 295/067* (2013.01); *C07D 401/04* (2013.01); *C07D 401/12* (2013.01)

(58) Field of Classification Search
None
See application file for complete search history.

(56) References Cited

U.S. PATENT DOCUMENTS

| | | |
|---|---|---|
| 2005/0009865 A1 | 1/2005 | Kudo et al. |
| 2005/0260126 A1 * | 11/2005 | Kudo et al. ................ 424/1.11 |
| 2010/0239496 A1 | 9/2010 | Gangadharmath |

FOREIGN PATENT DOCUMENTS

WO    WO 02085903 A2 *    10/2002

OTHER PUBLICATIONS

Patani et al. Chem. Rev. 1996, 96, 3147-3176.*
Watanabe et al. Bioorg. Med. Chem. 18 (2010) 4740-4746.*
Zhang et al. Curr. Top. Med. Chem. 2007, 7, 1817-1828.*
Wang, Journal of Labelled Compounds and Radiopharmaceuticals, vol. 36, No. 7, Jan. 1, 1995 pp. 671-678.
Okamura, et.al., Journal of Neuroscience, vol. 25, No. 47, Nov. 23, 2005 pp. 10857-10862.
Fuchimagi, et.al., Bioorganic & Medicinal Chemistry, vol. 17, No. 15, Aug. 1, 2009, pp. 5665-5675.
Scott, Chemical Abstracts Service, Database CA, Applied Radiation and Isotopes, vol. 67, 2009 pp. 88-94.
Matsumoto, et.al.Database Abstracts Service, Database Accession No. 2007:1004151 Abstract and Synapse pp. 759-800 2007.

* cited by examiner

*Primary Examiner* — Michael G Hartley
*Assistant Examiner* — Sean R Donohue
(74) *Attorney, Agent, or Firm* — Parks Wood LLC

(57) ABSTRACT

Heterocyclic compounds of formula (I) useful as imaging probes of Tau pathology in Alzheimer's disease are described. Compositions and methods of making such compounds are also described.

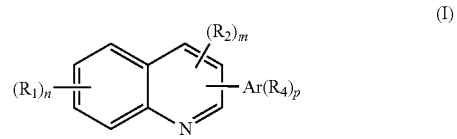

4 Claims, No Drawings

HETEROCYCLIC COMPOUNDS AS IMAGING PROBES OF TAU PATHOLOGY

TECHNICAL FIELD OF THE INVENTION

The present invention relates to radiolabeled quinoline and isoquinoline compounds, compositions thereof, methods of making such compounds and their use as imaging probes of Tau pathology especially as it relates to Alzheimer's Disease. Compounds of the present invention may be used for Positron Emission Tomography (PET) or Single Photon Emission Computed Tomography (SPECT) imaging.

DESCRIPTION OF RELATED ART

Alzheimer's disease (AD) is the most common cause of dementia in the elderly. It is definitively diagnosed and staged on the basis of post-mortem neuropathology. The pathological hallmark of AD is a substantial neuronal loss accompanied by deposition of amyloid plaques and neurofibrillary tangles (NFTs).

NFTs consist of filamentous aggregates composed of microtubule-associated protein tau. Much of the literature suggests that tau aggregates (NFTs) or NFT formation correlate more closely with AD progression than amyloid plaques (Braak, H. et al., Neuropathological Staging of Alzheimer-related Changes. *Acta Neuropathologica*, 82, 239-259, 1991). The tau aggregates or neurofibrillary lesions reportedly appear in areas (deep temporal lobe) decades before neocortical amyloid deposition and signs of dementia can be detected. The tau lesions occur before the presentation of clinical symptoms or signs of dementia and correlate with the severity of dementia. These attributes make tau aggregates a potentially superior approach for the early diagnosis of AD. Hence in vivo detection of these lesions or NFTs would prove useful for diagnosis of AD and for tracking disease progression.

One of the challenges in discovering NFT imaging probes is the selectivity for other protein aggregates (such as amyloid plaques) containing a cross beta-sheet conformation. Kudo et al. have recently screened compounds for selectivity to aggregated tau over amyloid in vitro. BF-170 and BF-158 were described as being ~threefold selective for tau aggregates over Aβ1-42 amyloid:

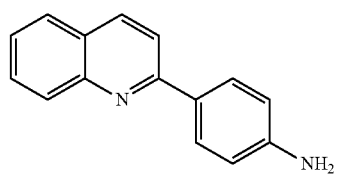

BF-170

Ec$_{50}$ (tau) = 221 nM
Ec$_{50}$ (amyloid) = 786 nM

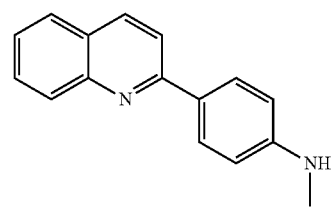

BF-158

Ec$_{50}$ (tau) = 399 nM
Ec$_{50}$ (amyloid) = 659 nM (Kudo, Y., et al., J. Neuroscience, 2005, 25(47):10857-10862). These compounds and other quinoline derivatives are also described in US 2005/0009865, now U.S. Pat. No. 7,118,730, as diagnostic probes for the imaging diagnosis of diseases in which tau protein accumulates. The probes can be labeled with a radionuclide.

However there still exist a need in the art for compounds that can be used as imaging agents for NFTs. The present invention described below answers such a need.

SUMMARY OF THE INVENTION

The present invention provides novel quinoline compounds for use as imaging probes of Tau pathology in Alzheimer's disease. The compounds of the inventions may be radiolabeled such that they may be used for in vitro and in vivo imaging purposes.

The present invention provides a compound of Formula I:

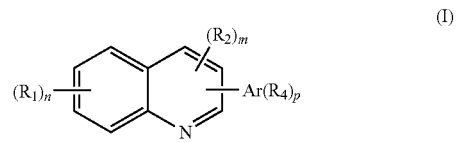

(I)

wherein:

$R_1$ is independently H, halogen, OH, COOH, SO$_3$H, NH$_2$, NO$_2$, CONHNH$_2$, alkyl, or alkoxy;

$R_2$ is independently H, halogen, OH, COOH, SO$_3$H, NH$_2$, NO$_2$, CONHNH$_2$, alkyl, or alkoxy;

$R_4$ is independently H or NR$_5$R$_6$ where R$_5$ and R$_6$ are each independently H, alkyl, haloalkyl, —(CH$_2$)$_q$OR$_7$, —(CH$_2$)$_q$O (CH$_2$)$_r$OR$_7$, —(CH$_2$)$_q$NR$_7$R$_8$, —(CH$_2$)$_q$aryl, —(CH$_2$)$_q$heteroaryl, —(CH$_2$)$_q$heterocyclyl, where R$_5$ and R$_6$ may be further optionally substituted with at least one group selected from the group consisting of —OH, —OR$_3$, N(R$_3$)$_2$, C(O) OR$_3$, C(O)N(R$_3$)$_2$, SO$_2$N(R$_3$)$_2$ where R$_3$ is independently H, alkyl, aryl, heteroaryl, heterocyclyl, cycloalkyl, wherein R$_3$ is further optionally substituted; or R$_5$ and R$_6$ taken together taken together with the nitrogen to which they are attached form a cyclic or aromatic moiety which optionally contains at least one other heteroatom selected from the group consisting of nitrogen, oxygen and sulfur and which is optionally substituted with at least one of halogen, OH, COOH, SO$_3$H, NH$_2$, NO$_2$, CONHNH$_2$, alkyl, or alkoxy;

$R_7$ and $R_8$ are each independently H, alkyl, —(CH$_2$)$_t$NR$_9$R$_{10}$ or R$_7$ and R$_8$ taken together with the nitrogen to which they are attached form a cyclic or aromatic moiety which optionally contains at least one other heteroatom selected from the group consisting of nitrogen, oxygen and sulfur;

$R_9$ and $R_{10}$ are each independently alkyl, H, —C(O)Ar, —C(O)NH(CH$_2$)$_w$NH$_2$, —C(O)alkyl;

n is an integer from 0-4;
m is an integer from 0-2;
p is an integer from 0-4;
q is an integer from 0-10;
t is an integer from 1-10;
w is an integer from 1-10;

Ar is an aryl, heteroaryl, cycloalkyl, heterocycloalkyl group optionally substituted with at least one of halogen, OH, COOH, SO$_3$H, NH$_2$, NO$_2$, CONHNH$_2$, alkyl, or alkoxy;

wherein at least one of R$_1$, R$_2$, R$_3$, R$_4$ and Ar is optionally a radionuclide or optionally substituted with a radionuclide; and with the proviso that said Compound of Formula (I) is not 2-(4-(amino)phenyl)quinoline (BF-170); 2-(4-(methylamino)phenyl)quinoline (BF-158); 2-(4-(dimethylamino) phenyl)quinoline (N-310); 2-(4-(diethylamino)phenyl) quinoline (N-313); 2-(4-aminophenyl)-6-bromo-4-carbazoylquinoline (N-311); potassium 2-(4-aminophenyl)-quinoline-4-carboxylate (N-312); or 2-(4-(dimethylamino) phenyl)-7-methylquinoline (SA-820).

The present invention further provides a pharmaceutical composition comprising a compound of Formula (I) and a pharmaceutically acceptable carrier or excipient.

The present invention further provides a method of making a compound of Formula (I).

The present invention further provides a method of imaging using a compound of Formula (I) or a pharmaceutical composition thereof.

The present invention further provides a method of detecting tau aggregates in vitro and/or vivo using a compound of Formula (I) or a pharmaceutical composition thereof.

DETAILED DESCRIPTION OF THE INVENTION

The present invention provides quinoline compounds of Formula (I) as described herein.

In a preferred embodiment of the invention, a compound of Formula (I), as described above, is provided wherein Ar is selected from the group consisting of:

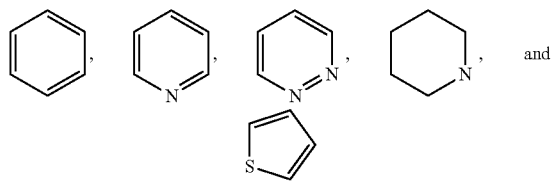

with the proviso that when Ar is a phenyl group said Compound of Formula (I) is not 2-(4-(amino)phenyl)quinoline (BF-170); 2-(4-(methylamino)phenyl)quinoline (BF-158); 2-(4-(dimethylamino)phenyl)quinoline (N-310); 2-(4-(diethylamino)phenyl)quinoline (N-313); 2-(4-aminophenyl)-6-bromo-4-carbazoylquinoline (N-311); potassium 2-(4-aminophenyl)-quinoline-4-carboxylate (N-312); or 2-(4-(dimethylamino)phenyl)-7-methylquinoline (SA-820).

The present invention provides a compound of Formula (I) having Formula (Ia):

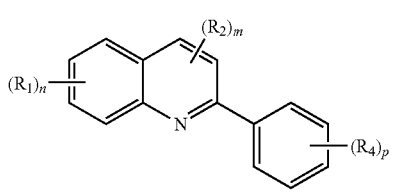

wherein $R_1$, $R_2$, $R_4$, n, m and p are each as defined herein for a compound of Formula (I) with the proviso that said Compound of Formula (Ia) is not 2-(4-(amino)phenyl)quinoline (BF-170); 2-(4-(methylamino)phenyl)quinoline (BF-158); 2-(4-(dimethylamino)phenyl)quinoline (N-310); 2-(4-(diethylamino)phenyl)quinoline (N-313); 2-(4-aminophenyl)-6-bromo-4-carbazoylquinoline (N-311); potassium 2-(4-aminophenyl)-quinoline-4-carboxylate (N-312); or 2-(4-(dimethylamino)phenyl)-7-methylquinoline (SA-820).

The present invention provides a compound of Formula (I) having Formula (II):

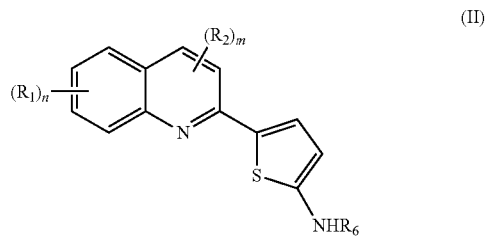

wherein $R_1$, $R_2$, n and m are each as defined herein for a compound of Formula (I) and $R_6$ is H, Me, or $CH_2CH_2F$.

The present invention provides a compound of Formula (I) having Formula (III):

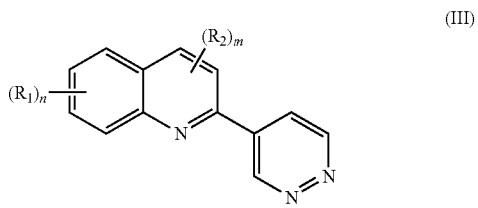

wherein $R_1$, $R_2$, n and m are each as defined herein for a compound of Formula (I).

The present invention provides a compound of Formula (I) having Formula (IV):

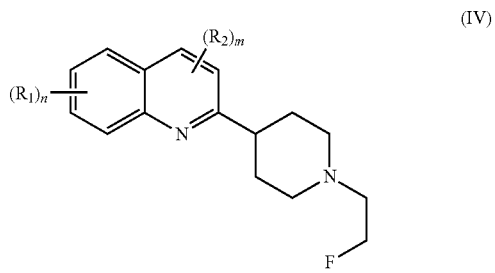

wherein $R_1$, $R_2$, n and m are each as defined herein for a compound of Formula (I).

The present invention provides a compound of Formula (I) having Formula (V):

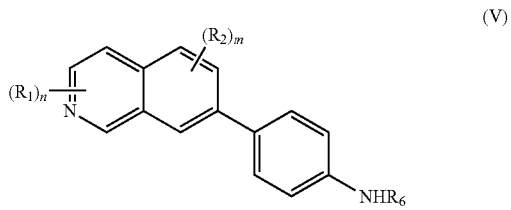

wherein $R_1$, $R_2$, n and m are each as defined herein for a compound of Formula (I) and $R_6$ is H, Me, or $CH_2CH_2F$.

The present invention provides a compound of Formulae (VI) and (VIa):

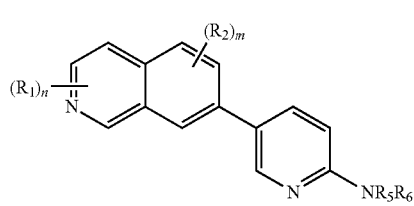

(VI)

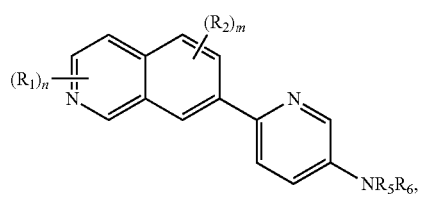

(VIa)

wherein $R_1$, $R_2$, $R_5$, $R_6$, n and m are each as defined herein for a compound of Formula (I).

The present invention provides a compound of Formulae (VII) and (VIIa):

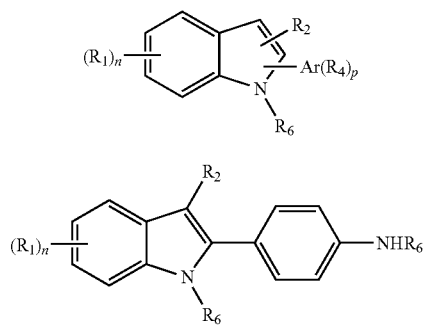

(VII)

(VIIa)

wherein $R_1$, $R_2$, $R_4$, $R_6$, Ar, n, m and p found in Formulae (VII) and (VIIa) are each as defined herein for a compound of Formula (I).

The present invention provides a compound of Formulae (VIII) and (VIIIa):

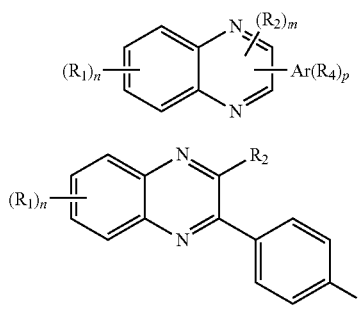

(VIII)

(VIIIa)

wherein $R_1$, $R_2$, $R_4$, Ar, n, m and p found in Formulae (VIII) and (VIIIa) are each as defined herein for a compound of Formula (I).

The present invention provides a compound of Formulae (IX) and (IXa):

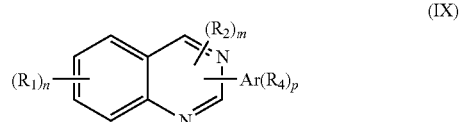

(IX)

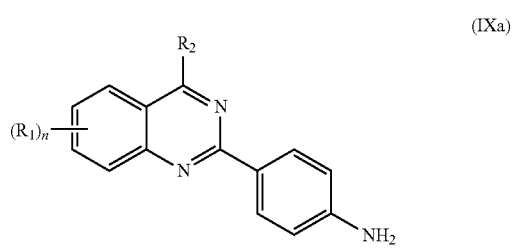

(IXa)

wherein $R_1$, $R_2$, $R_4$, Ar, n, m and p found in Formulae (IX) and (IXa) are each as defined herein for a compound of Formula (I).

The present invention provides a compound of Formula (I) selected from the group consisting of:

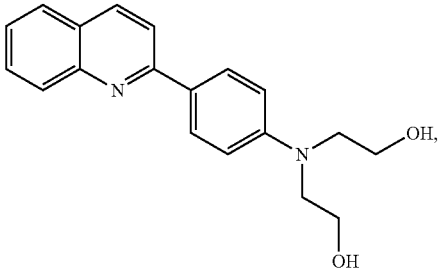

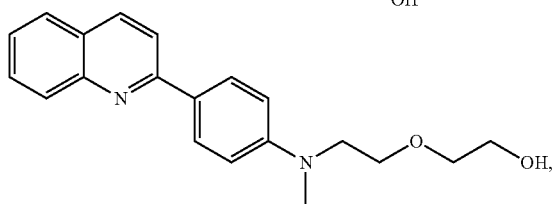

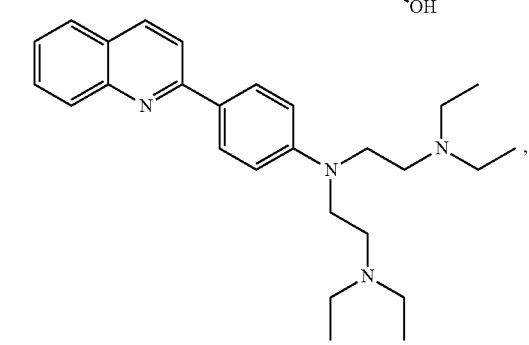

-continued
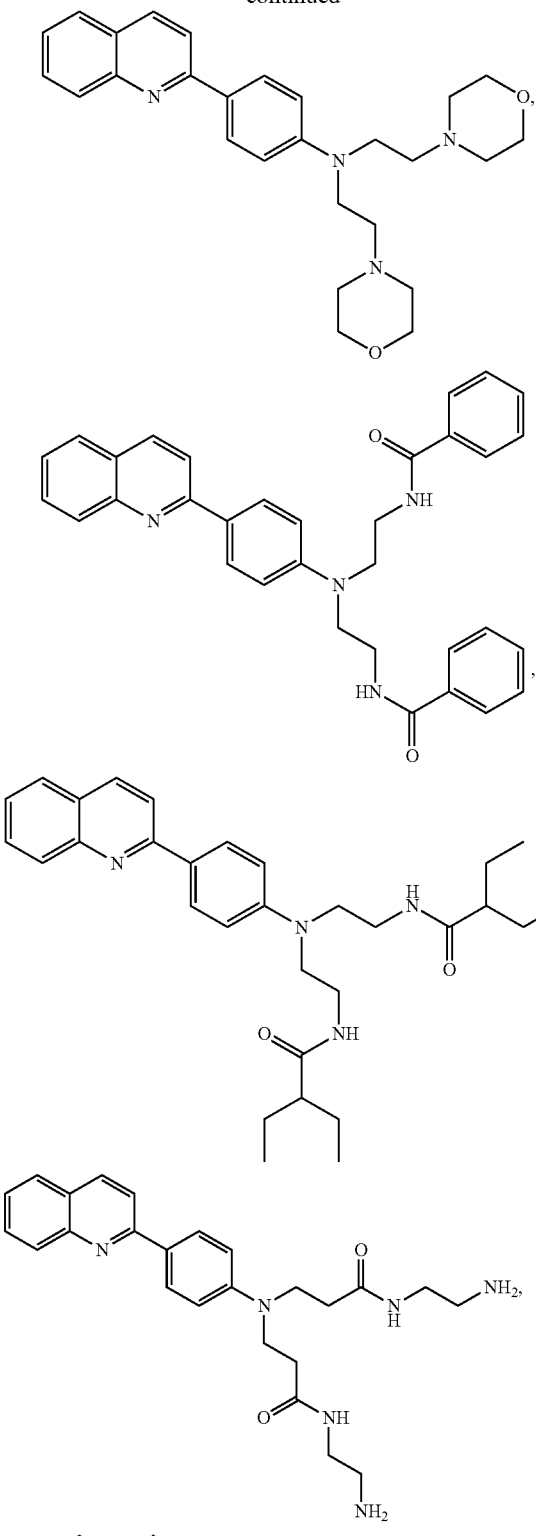
The present invention provides a compound of Formula (I) selected from the group consisting of:
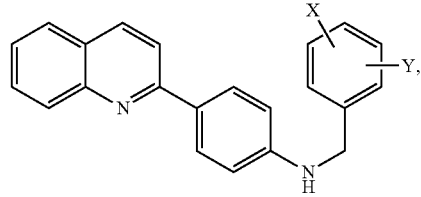
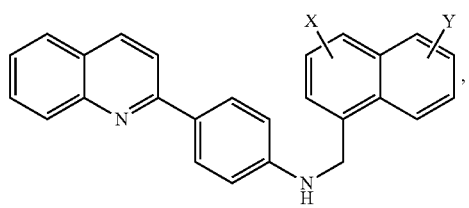
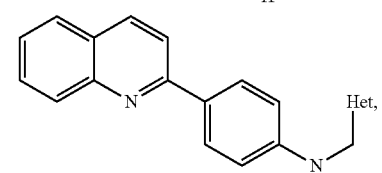
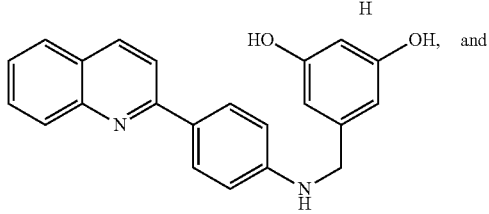
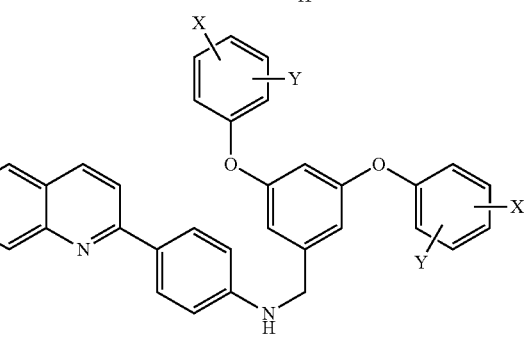
wherein X and Y are each independently OH, $OR_3$, $N(R_3)_2$, $CO_2R$, $CO_2N(R_3)_2$ or $SO_2N(R_3)_2$ where $R_3$ is as defined herein; and Het is a heterocyclic group.
The present invention provides a compound of Formula (I) selected from the group consisting of:
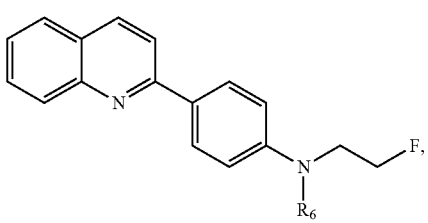

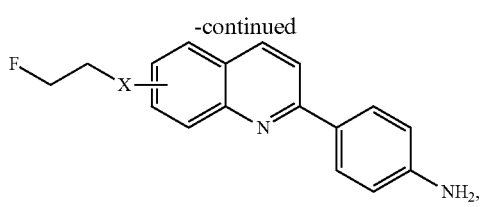
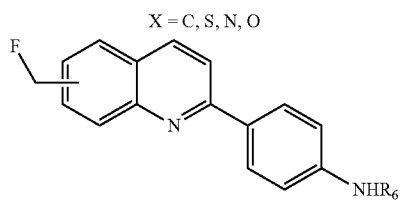
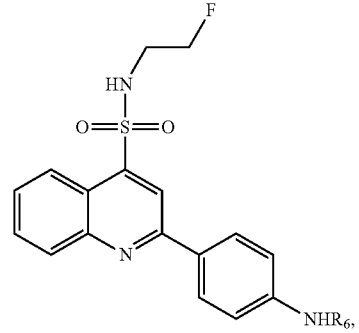
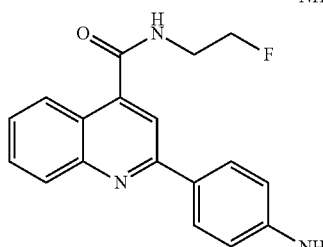
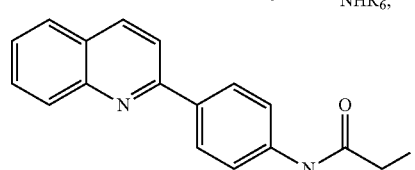
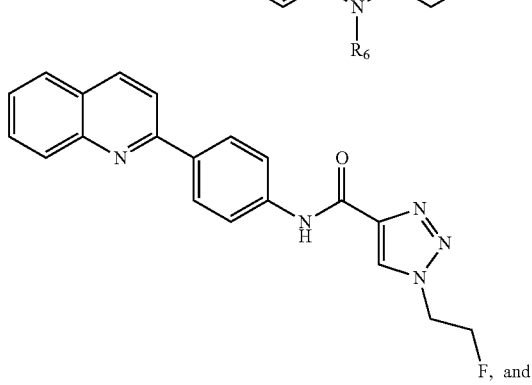
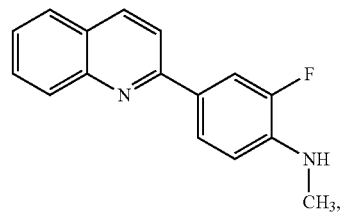
wherein "F" of each of the structures can be either cold fluorine (F) or radioisotopic fluorine (e.g. $^{18}$F) and $R_6$ is as defined for a compound of Formula (I).
The present invention provides a compound of Formula (I) selected from the group consisting of:
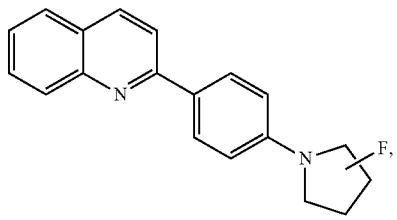
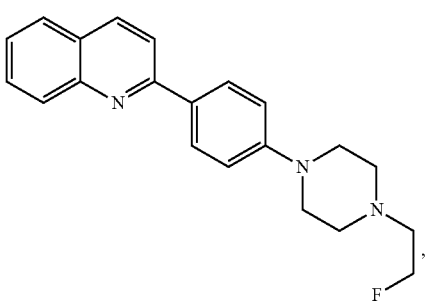
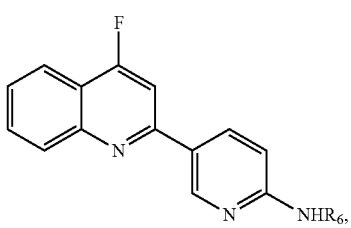
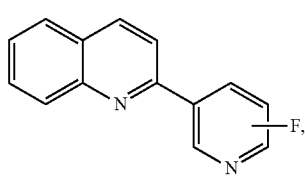
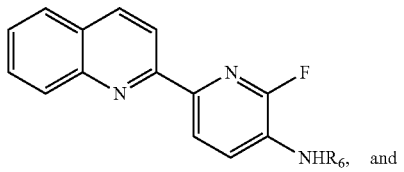
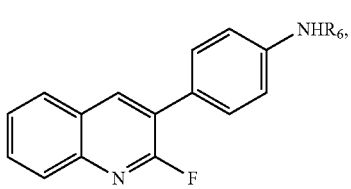
wherein $R_6$ is as defined for a compound of Formula (I).

According to the present invention, for a compound of the invention described herein, a halogen is selected from F, Cl, Br, and I; preferably, F.

According to the present invention, for a compound of the invention described herein, a radionuclide shall mean any radioisotope known in the art (hereinafter referred to as a "radiolabeled compound"). Preferably the radionuclide is a radioisotope suitable for imaging (e.g., PET, SPECT). In one embodiment, the radionuclide is a radioisotope suitable for PET imaging. Even more preferably, the radionuclide is $^{11}$C, $^{13}$N, $^{15}$O, $^{68}$Ga, $^{62}$Cu, $^{18}$F, $^{76}$Br, $^{124}$I, or $^{125}$I; even more preferably, the radionuclide is $^{18}$F.

In one embodiment, the radionuclide is a radioisotope suitable for SPECT imaging. Even more preferably, the radionuclide is $^{99m}$Tc, $^{111}$In, $^{67}$Ga, $^{201}$Tl, $^{123}$I, or $^{133}$Xe; even more preferably, the radionuclide is $^{99m}$Tc or $^{123}$I.

Pharmaceutical or Radiopharmaceutical Composition

The present invention provides a pharmaceutical or radiopharmaceutical composition comprising a compound of the invention as described herein together with a pharmaceutically acceptable carrier, excipient, or biocompatible carrier. According to the invention when a compound of the invention is radiolabeled with a radionuclide, the pharmaceutical composition is a radiopharmaceutical composition.

The present invention further provides a pharmaceutical or radiopharmaceutical composition comprising a compound of the invention as described herein together with a pharmaceutically acceptable carrier, excipient, or biocompatible carrier suitable for mammalian administration.

As would be understood by one of skill in the art, the pharmaceutically acceptable carrier or excipient can be any pharmaceutically acceptable carrier or excipient known in the art.

The "biocompatible carrier" can be any fluid, especially a liquid, in which a compound of the invention can be suspended or dissolved, such that the pharmaceutical composition is physiologically tolerable, e.g., can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (e.g., salts of plasma cations with biocompatible counterions), sugars (e.g., glucose or sucrose), sugar alcohols (e.g., sorbitol or mannitol), glycols (e.g., glycerol), or other non-ionic polyol materials (e.g., polyethyleneglycols, propylene glycols and the like). The biocompatible carrier may also comprise biocompatible organic solvents such as ethanol. Such organic solvents are useful to solubilise more lipophilic compounds or formulations. Preferably the biocompatible carrier is pyrogen-free water for injection, isotonic saline or an aqueous ethanol solution. The pH of the biocompatible carrier for intravenous injection is suitably in the range 4.0 to 10.5.

The pharmaceutical or radiopharmaceutical composition may be administered parenterally, i.e., by injection, and is most preferably an aqueous solution. Such a composition may optionally contain further ingredients such as buffers; pharmaceutically acceptable solubilisers (e.g., cyclodextrins or surfactants such as Pluronic, Tween or phospholipids); pharmaceutically acceptable stabilisers or antioxidants (such as ascorbic acid, gentisic acid or para-aminobenzoic acid). Where a compound of the invention is provided as a radiopharmaceutical composition, the method for preparation of said compound may further comprise the steps required to obtain a radiopharmaceutical composition, e.g., removal of organic solvent, addition of a biocompatible buffer and any optional further ingredients. For parenteral administration, steps to ensure that the radiopharmaceutical composition is sterile and apyrogenic also need to be taken. Such steps are well-known to those of skill in the art.

Preparation of a Compound of the Invention

A compound of the invention may be prepared by any means known in the art including, but not limited to, nucleophilic aromatic substitution, nucleophilic aliphatic substitution, and click chemistry.

In one embodiment of the invention, a compound of the invention may be halogenated or radiolabeled with a radionuclide by nucleophilic aromatic substitution or nucleophilic aliphatic substitution of an appropriate leaving group with the desired halogen or radionuclide. Examples of suitable leaving groups for nucleophilic aromatic substitution include, but are not limited to, Cl, Br, F, NO$_2$ and $^+$N(R)$_4$. Examples of suitable leaving groups for nucleophilic aliphatic substitution include, but are not limited to, I, Br, Cl, and OTs (tosylate).

In one embodiment, a compound of the invention may be prepared by means of the Suzuki reaction viz:

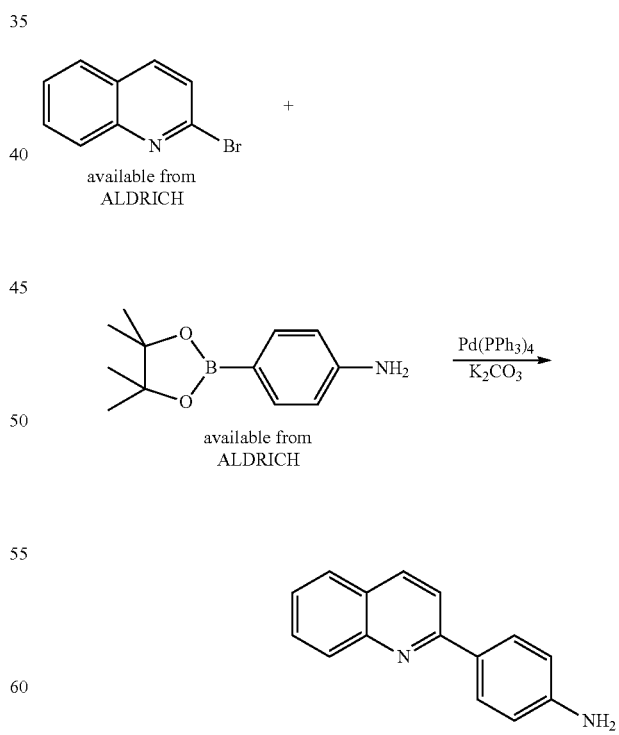

Isoquinoline compounds of the invention may be prepared in a similar fashion starting with bromo-isoquinoline.

In one embodiment, a compound of the invention may be prepared according to the following Scheme I:

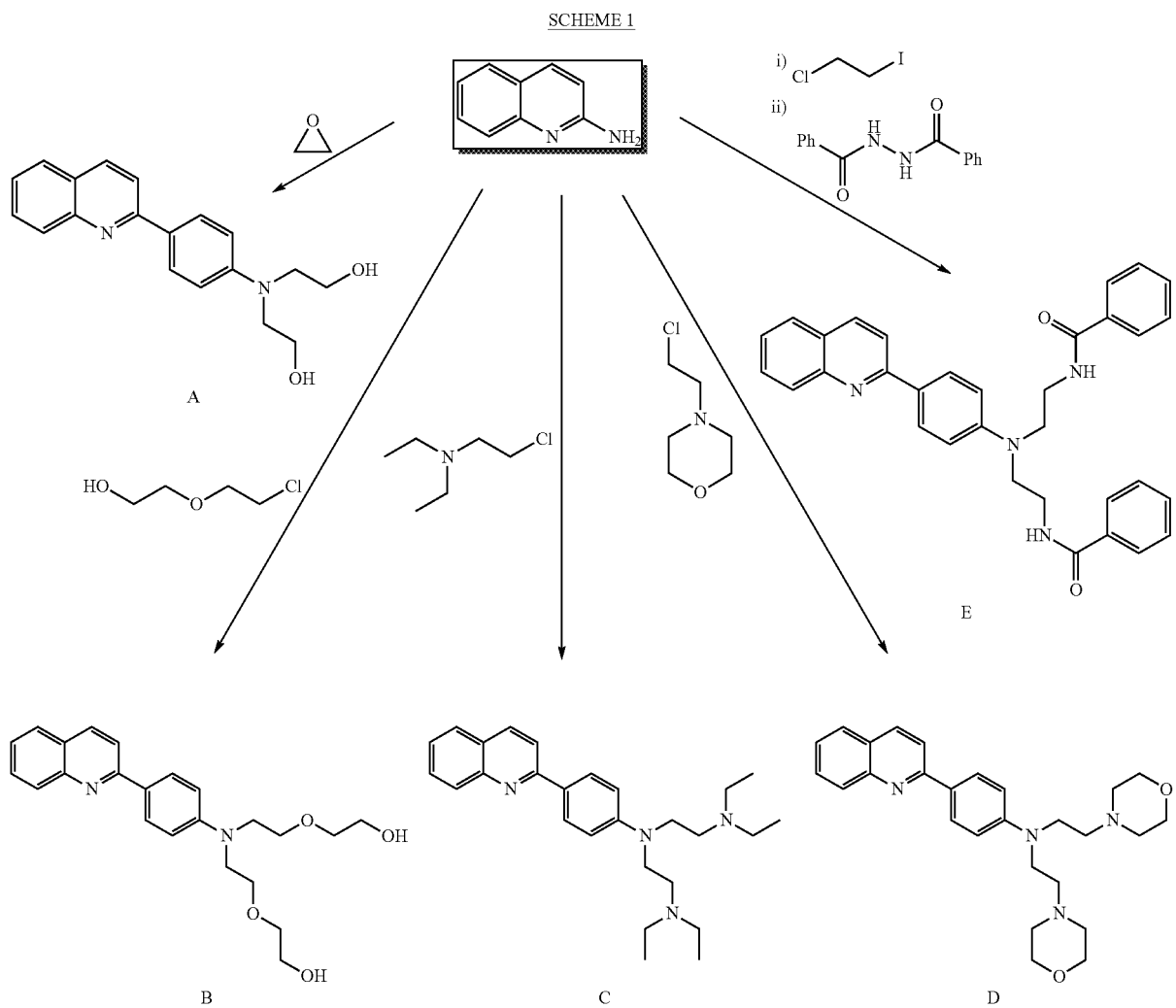

Substituted bulky aromatic groups could also be attached to the aniline

In one embodiment, a compound of the invention may be prepared via reductive amination with aniline and substituted aldehydes:

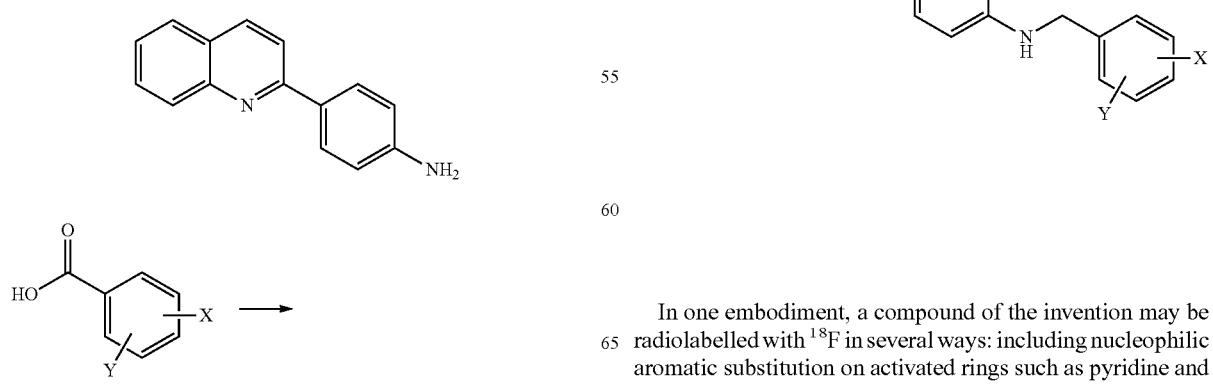

In one embodiment, a compound of the invention may be radiolabelled with $^{18}F$ in several ways: including nucleophilic aromatic substitution on activated rings such as pyridine and quinoline and nucleophilic aliphatic substitution viz:

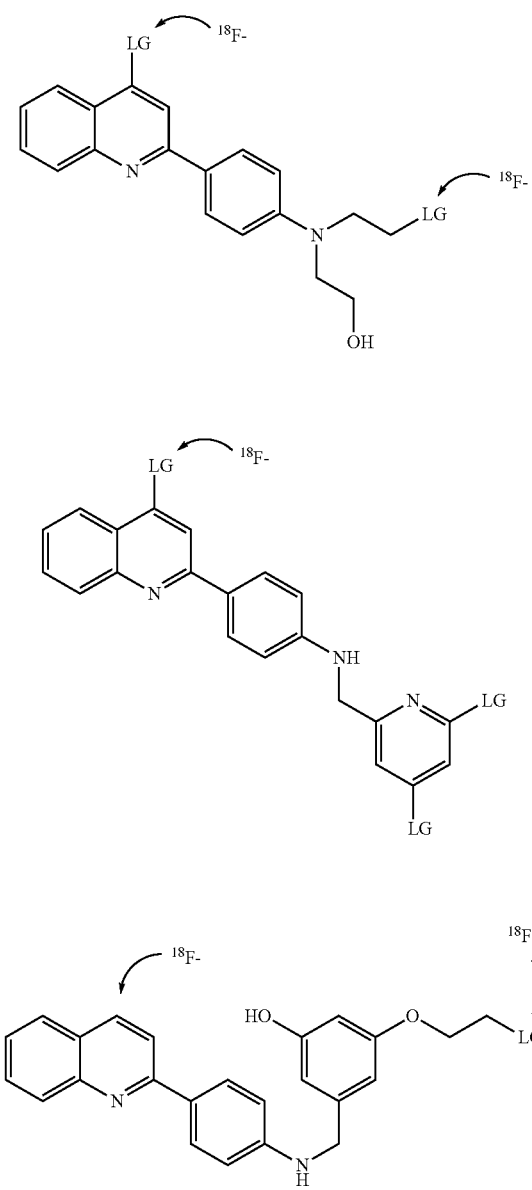

LG = NO₂, Cl, ⁺NR₃, OTs

By way of example, the radioisotope [¹⁸F]-fluoride ion (¹⁸F⁻) is normally obtained as an aqueous solution from the nuclear reaction ¹⁸O(p,n)¹⁸F and is made reactive by the addition of a cationic counterion and the subsequent removal of water. Suitable cationic counterions should possess sufficient solubility within the anhydrous reaction solvent to maintain the solubility of 18F⁻. Therefore, counterions that have been used include large but soft metal ions such as rubidium or caesium, potassium complexed with a cryptand such as Kryptofix™, or tetraalkylammonium salts. A preferred counterion is potassium complexed with a cryptand such as Kryptofix™ because of its good solubility in anhydrous solvents and enhanced ¹⁸F⁻ reactivity. ¹⁸F can also be introduced by nucleophilic displacement of a suitable leaving group such as a halogen or tosylate group. A more detailed discussion of well-known ¹⁸F labelling techniques can be found in Chapter 6 of the "Handbook of Radiopharmaceuticals" (2003; John Wiley and Sons: M. J. Welch and C. S. Redvanly, Eds.). Similar methods may be used to radiolabel a compound of the invention with other radioisotopes including the PET and SPECT radioisotopes described herein.

Automated Synthesis

In one embodiment, the method to prepare a radiolabeled compound of the invention, each as described herein, is automated. For example, [¹⁸F]-labeled compounds of the invention may be conveniently prepared in an automated fashion by means of an automated radiosynthesis apparatus. There are several commercially-available examples of such platform apparatus, including TRACERlab™ (e.g., TRACERlab™ MX) and FASTlab™ (both from GE Healthcare Ltd.). Such apparatus commonly comprises a "cassette", often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges used in post-radiosynthetic clean up steps. Optionally, in a further embodiment of the invention, the automated radiosynthesis apparatus can be linked to a high performance liquid chromatograph (HPLC). The present invention therefore provides a cassette for the automated synthesis of a compound of the invention.

Imaging Method

The radiolabeled compound of the invention, as described herein, may bind to NFTs or tau aggregates and aid in identifying the amount of NFTs/tau aggregates present which in turn may correlate with the stage of AD.

The present invention thus provides a method of imaging comprising the step of administering a radiolabeled compound of the invention, as described herein, to a subject and detecting said radiolabeled compound of the invention in said subject. The present invention further provides a method of detecting tau aggregates in vitro or in vivo using a radiolabeled compound of the invention, as described herein. Hence the present invention provides better tools for early detection and diagnosis of Alzheimers disease. The present invention also provides better tools for monitoring the progression of Alzheimers disease and the effect of treatment.

As would be understood by one of skill in the art the type of imaging (e.g., PET, SPECT) will be determined by the nature of the radioisotope. For example, if the radiolabeled compound of the invention contains ¹⁸F it will be suitable for PET imaging.

Thus the invention provides a method of detecting tau aggregates in vitro or in vivo comprising the steps of:
  i) administering to a subject a radiolabeled compound of the invention as defined herein;
  ii) allowing said a radiolabeled compound of the invention to bind to NFTs in said subject;
  iii) detecting signals emitted by said radioisotope in said bound radiolabeled compound of the invention;
  iv) generating an image representative of the location and/or amount of said signals; and,
  v) determining the distribution and extent of said tau aggregates in said subject.

The step of "administering" a radiolabeled compound of the invention is preferably carried out parenterally, and most preferably intravenously. The intravenous route represents the most efficient way to deliver the compound throughout the body of the subject. Intravenous administration neither represents a substantial physical intervention nor a substantial health risk to the subject. The radiolabeled compound of the invention is preferably administered as the radiopharmaceutical composition of the invention, as defined herein. The administration step is not required for a complete definition of the imaging method of the invention. As such, the imaging method of the invention can also be understood as comprising the above-defined steps (ii)-(v) carried out on a subject to whom a radiolabeled compound of the invention has been pre-administered.

Following the administering step and preceding the detecting step, the radiolabeled compound of the invention is allowed to bind to the tau aggregates. For example, when the subject is an intact mammal, the radiolabeled compound of the invention will dynamically move through the mammal's body, coming into contact with various tissues therein. Once the radiolabeled compound of the invention comes into contact with the tau aggregates it will bind to the tau aggregates.

The "detecting" step of the method of the invention involves detection of signals emitted by the radioisotope comprised in the radiolabeled compound of the invention by means of a detector sensitive to said signals, e.g., a PET camera. This detection step can also be understood as the acquisition of signal data.

The "generating" step of the method of the invention is carried out by a computer which applies a reconstruction algorithm to the acquired signal data to yield a dataset. This dataset is then manipulated to generate images showing the location and/or amount of signals emitted by the radioisotope. The signals emitted directly correlate with the amount of enzyme or neoplastic tissue such that the "determining" step can be made by evaluating the generated image.

The "subject" of the invention can be any human or animal subject. Preferably the subject of the invention is a mammal. Most preferably, said subject is an intact mammalian body in vivo. In an especially preferred embodiment, the subject of the invention is a human.

The "disease state associated with the tau aggregates" can be MC1 (mild cognitive impairment), dementia or Alzheimers disease.

All patents, journal articles, publications and other documents discussed and/or cited above are hereby incorporated by reference.

What is claimed is:

1. A compound of Formula (IV):

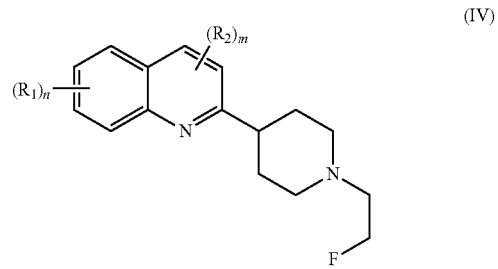

wherein $R_1$ is independently H, halogen, OH, COOH, $SO_3H$, $NH_2$, $NO_2$, $CONHNH_2$, alkyl, or alkoxy;

$R_2$ is independently H, halogen, OH, COOH, $SO_3H$, $NH_2$, $NO_2$, $CONHNH_2$, alkyl, or alkoxy;

n is an integer from 0-4; and m is an integer from 0-2;

wherein at least one of $R_1$ and $R_2$ is optionally a radionuclide or optionally substituted with a radionuclide; and wherein F is optionally $^{18}F$.

2. A pharmaceutical composition comprising a compound according claim 1 and a pharmaceutically acceptable carrier or excipient.

3. A method of imaging comprising administering a compound of claim 1 wherein said $R_1$ or $R_2$ is a radionuclide or substituted with a radionuclide or the F of the compound of Formula (IV) is $^{18}F$ or a pharmaceutical composition thereof.

4. A method of detecting tau aggregates and/or in vivo comprising the steps of:
   i) administering to a subject a radiolabeled compound of claim 1, or a pharmaceutical composition thereof;
   ii) allowing said radiolabeled compound to bind to NFTs in said subject;
   iii) detecting signals emitted by said radiolabeled compound;
   iv) generating an image representative of the location and/or amount of said signals; and,
determining the distribution and extent of said tau aggregates in said subject.

* * * * *